United States Patent
Billingham et al.

(10) Patent No.: US 8,105,534 B2
(45) Date of Patent: Jan. 31, 2012

(54) PROCESS AND SYSTEM FOR PURIFYING GASES

(75) Inventors: John Fredric Billingham, Getzville, NY (US); Jerry Michael Mahl, Youngstown, NY (US)

(73) Assignee: Praxair Technology, Inc., Danbury, CT (US)

( * ) Notice: Subject to any disclaimer, the term of this patent is extended or adjusted under 35 U.S.C. 154(b) by 1373 days.

(21) Appl. No.: 11/483,105

(22) Filed: Jul. 10, 2006

(65) Prior Publication Data
US 2006/0251545 A1    Nov. 9, 2006

Related U.S. Application Data

(62) Division of application No. 10/174,819, filed on Jun. 20, 2002, now Pat. No. 7,097,689.

(51) Int. Cl.
| | | |
|---|---|---|
| G01N 21/00 | (2006.01) | |
| G01N 31/00 | (2006.01) | |
| G01N 33/00 | (2006.01) | |
| G01N 15/06 | (2006.01) | |
| G01N 33/48 | (2006.01) | |
| B01D 53/30 | (2006.01) | |
| F01N 3/20 | (2006.01) | |
| G05B 1/00 | (2006.01) | |
| B01J 19/00 | (2006.01) | |
| B01J 10/00 | (2006.01) | |
| B01J 10/02 | (2006.01) | |
| B01J 12/00 | (2006.01) | |
| B01J 12/02 | (2006.01) | |
| B01J 14/00 | (2006.01) | |
| B01J 15/00 | (2006.01) | |
| B01J 16/00 | (2006.01) | |
| G05D 7/00 | (2006.01) | |

(52) U.S. Cl. ......... 422/62; 422/68.1; 422/105; 422/108; 422/110; 422/129; 95/12

(58) Field of Classification Search ................. 422/68.1; 95/12

See application file for complete search history.

(56) References Cited

U.S. PATENT DOCUMENTS

| | | | | |
|---|---|---|---|---|
| 3,897,226 | A * | 7/1975 | Doherty | 95/12 |
| 5,150,604 | A | 9/1992 | Succi et al. | 73/38 |
| 5,238,469 | A * | 8/1993 | Briesacher et al. | 95/115 |
| 5,265,031 | A | 11/1993 | Malczewski | 364/497 |
| 5,334,237 | A * | 8/1994 | Lorimer | 95/25 |
| 5,669,961 | A * | 9/1997 | Baker et al. | 95/115 |
| 5,917,066 | A | 6/1999 | Eisenmann et al. | 55/502 |
| 6,068,685 | A | 5/2000 | Lorimer et al. | 96/112 |
| 6,156,105 | A | 12/2000 | Lorimer et al. | 96/112 |
| 6,168,645 | B1 | 1/2001 | Succi et al. | 95/8 |
| 6,514,313 | B1 * | 2/2003 | Spiegelman et al. | 95/23 |

* cited by examiner

*Primary Examiner* — In Suk Bullock
*Assistant Examiner* — Bryan Kilpatrick
(74) *Attorney, Agent, or Firm* — Nilay S. Dalal; Iurie A. Schwartz

(57) ABSTRACT

A process and system for purifying an impure gas to produce a purified gas in a gas purification system and protecting the system from damage by a) passing a portion of a first gas stream into a reactor vessel, which exits as a second purified gas stream; b) combining a portion of the second purified gas stream with another portion of the first gas stream to form a combined gas stream; and c) passing the combined gas stream into a sensing device to regulate the flow of the first and second gas streams into the reactor vessel.

10 Claims, 2 Drawing Sheets

Process according to the invention

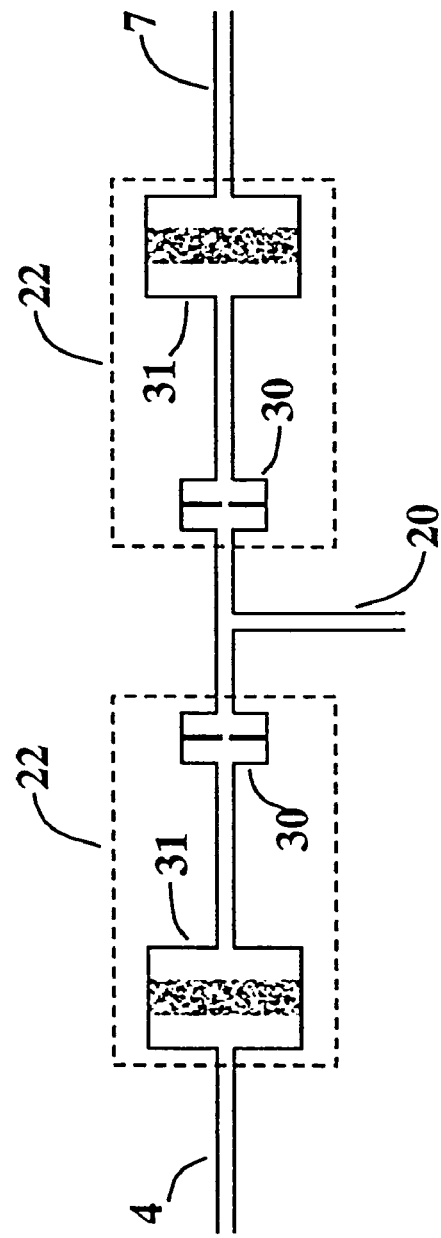
Figure 1  Flow metering device utilizing critical flow orifices protected by inline filters

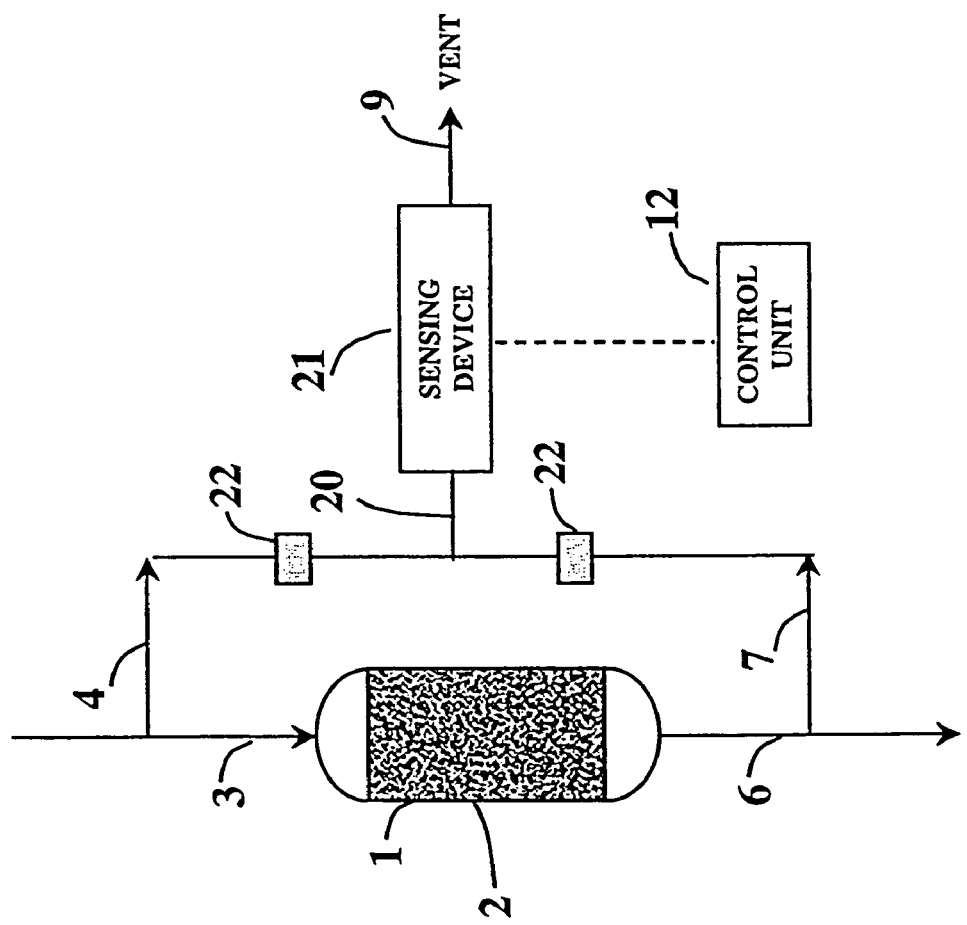
Figure 2  Process according to the invention

PROCESS AND SYSTEM FOR PURIFYING GASES

RELATED APPLICATIONS

This application is a divisional of prior U.S. application Ser. No. 10/174,819, filed Jun. 20, 2002 now U.S. Pat. No. 7,097,689.

FIELD OF THE INVENTION

This invention generally relates to a process and system for protecting a gas purification system from damage. In particular, this invention is directed to a process and system for operating an ultra high purity gas purifier using a getter while minimizing the chance for damage to the gas purification system.

BACKGROUND OF THE INVENTION

Ultra-high purity (UHP) gas purification systems are generally used to supply customers with UHP nitrogen. The initial source of nitrogen (the distillation plant, or the liquid nitrogen supply) typically contains about 1 ppm oxygen by volume. The oxygen level is monitored by an oxygen analyzer before passing into the gas purification vessel, which contains material that reacts with impurities in the nitrogen to produce purified gas.

Ultra-high purity inert gas purification systems generally employ a getter metal that is comminuted by some means, and then dispersed in a matrix of a comparatively inert substrate material (usually alumina or similar). Once activated by a reduction process of some kind, this high surface area metal can then react extremely rapidly with various impurity gases (oxygen, hydrogen and others, depending on the getter material and temperature) to chemically bond with reactive gases, and so remove them from the gas stream: a process known as chemisorption.

The speed of the reaction, plus its highly exothermic (heat-evolving) nature means that processing inert gases containing high levels of a reactive impurity may cause significant damage and personal danger. For example, it is known that exposing activated nickel-based getters to oxygen concentrations greater than 1% by volume (10,000 ppm $O_2$) will generally cause heat-damage to the getter bed, and possibly also to the reactor vessel and downstream customer equipment. The cost of the damage in such an instance ranges from tens of thousands to millions of dollars, when the impact on downstream processing is accounted for.

It is therefore a priority to ensure that such instances are avoided. As such, safety schemes have been devised to protect the bed from excessive levels of contaminant, and thus excessively high temperatures.

One safety scheme is to measure the temperature of the bed using judiciously placed temperature measuring devices, such as thermocouples. If the bed temperature rises due to the exothermic reactions, action is taken to safeguard the bed. This action will typically consist of diverting the feed gas and venting the purifier to rid it of remaining reactive gases and preventing additional reactive gases from entering. This will typically be performed automatically using a control unit that recognizes that a temperature setpoint has been reached and actuates valves to the shutdown condition. A major problem with this approach is that it requires that the bed be exposed to high levels of reactive impurities before action is taken, since this is necessary to raise the temperature of the bed.

Another safety scheme is to sample the gas stream prior to entering the bed. When a predetermined level of contaminants is reached, typically orders of magnitude above that normally present in the feed gas, action is taken to safeguard the bed. There are several types of measuring device. Typically, commercially available gas analyzers can be used. The approach of measuring the gas stream prior to entering the bed has the advantage that it can potentially react more rapidly than thermocouples placed inside the purifier that is being protected, i.e. it can take action to safeguard the bed before the bed is exposed to high levels of reactive species. Further, it is possible to detect levels of reactive species that are higher than normal operation but are below that required to raise the temperature of the bed significantly. Thus it is possible to design a system that is more sensitive to reactive species than one that simply embeds thermocouples inside the purifier bed and waits for these to register an increase in temperature.

One drawback to this approach is the cost of the unit, both in terms of the initial purchase cost and the maintenance required to keep the analyzer in good working order. For example, oxygen is commonly the species that the purifier must be protected from. Two standard varieties of oxygen-detection cell provide an electrical current output from either (i) a cell that operates at ambient temperature, containing salt solution that needs to be maintained at a fairly constant level by continuous replenishment with deionized water or new salt solution, or (ii) a zirconia ($ZrO_2$) cell maintained at high temperature (typically greater than 600° C.), that has a typical lifetime of two years or less.

The cost of using analysis external to the bed is compounded by the need to protect the gas from a backflow condition. Backflow may occur due to errors in operation or piping hook-up, or as a result of upset conditions that cause the pressure within the purifier to be lower than the pressure downstream and thus cause gas to enter the bed in a direction counter to that during normal operation. Protection against backflow requires that both the streams entering and leaving the purifier must be sampled. This increases cost and reduces system reliability by requiring two measuring devices as opposed to one. The cost and reliability implication of monitoring the purifier both upstream and downstream is the problem that this current invention addresses.

U.S. Pat. Nos. 6,068,685 and 6,156,105 disclose the need to protect the purifier both upstream and downstream. A first temperature sensor is disposed in a top portion of the getter material that constitutes the purifier bed. The first temperature sensor is located in a melt zone to detect rapidly the onset of an exothermic reaction which indicates the presence of excess impurities in the incoming gas to be purified. A second temperature sensor is disposed in a bottom portion of the getter material. The second temperature sensor is located in a melt zone to detect rapidly the onset of an exothermic reaction which indicates that excess impurities are being backfed into the getter column. In these patents, a purifier vessel contains getter material. A gas stream enters the purifier vessel and a separate stream exits from the vessel. A thermocouple is placed at the inlet side of the bed. Another thermocouple is located near the exit of the bed. The temperature at both locations is sent to a control unit. The registered temperatures are compared with setpoint values. Action is taken to protect the bed if the setpoint is exceeded in either thermocouple.

U.S. Pat. No. 6,168,645B1 also discloses the need to protect the purifier both upstream and downstream. A first safety device is located upstream of a purifier and a second safety device is located downstream of the purifier. A sample stream is drawn from the feed stream, upstream of the purifier, and sent to an upstream safety device. Similarly, a sample stream is drawn downstream of the purifier and sent to the downstream safety device. The level of reactive species is sent from both safety devices to the control unit. If either safety device registers levels of reactive species is in excess of some defined setpoint, action is taken to safeguard the bed. On passing through the safety devices, the sample streams are typically sent to vent. Since this represents loss of product gas, there is a motivation to minimize the quantity of sample streams withdrawn.

Also disclosed in the '645 patent are low cost means of measuring the quantity of reactive species in the stream downstream of the purifier. In one embodiment, the safety device is simply a small sample of the getter material inside the purifier. The temperature rise in this guard bed is used as an indicator of the level of reactive species. Such an approach is not suitable for monitoring the upstream case because the level of reactive species is such that the bed material would react with the oxygen over time and thus become inert to the presence of additional reactive species. For example, activated nickel getter, commonly used to remove oxygen, hydrogen and carbon monoxide from bulk inert gases, has a limited capacity to react with oxygen, hydrogen and other impurities. The oxidation reaction is:

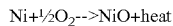

Once all the nickel has reacted in this way, there will be no further heat output by the purification material, no matter how high the oxygen concentration in gas or other fluid passing over it.

It is believed that the number of patents describing safety schemes for getter-based purifiers is limited. A series of patents disclose determining the end-of-life of a purifier, meaning the point at which the purifier allows unacceptable concentrations of impurities to break through. U.S. Pat. No. 5,150,604 discloses the use of pressure drop across the bed to determine the end of its useful life. The '604 patent discloses pressure transmitters that are located up and downstream of the purifier. The signals from these transmitters are sent to a control device to see if the pressure drop is above some setpoint.

There is therefore a need in the art to provide for a low cost and reliable process or system for monitoring the purifier both upstream and downstream of the getter.

SUMMARY OF THE INVENTION

This invention is directed to a process for purifying an impure gas to produce a purified gas in a gas purification system and protecting the system from damage comprising: a) passing a portion of a first gas stream into a reactor vessel, which exits as a second purified gas stream; b) passing a portion of the second purified gas stream to combine with another portion of the first gas stream to form a combined gas stream; and c) passing the combined gas stream into a sensing device to regulate the flow of the first gas stream into the reactor vessel.

This invention is also directed to a system for purifying a gas to produce a purified gas and protecting a reactor vessel in the system from damage comprising a) a reactor vessel; b) a first impure gas passing through the reactor vessel; c) a second purified gas which emerges from the reactor vessel as a product; d) a sensing device which passes information to a control unit; and e) a plurality of metering devices to combine and regulate the flow of the first impure gas and second purified gas and to direct the combined gases to the sensing device so that the control unit can control the flow of the first impure gas through the reactor vessel.

The sensing device has a control device to regulate the flows of the first and second gas streams. The combined gas stream passes through the sensing device and exits to vent.

The reactor vessel contains a getter to remove contaminant gases, primarily oxygen and other reactive gases, but which may also include other gases that are not reactive. The getter may also act as a catalyst. At least one flow meter device is used to monitor the flow of gases.

In one embodiment, the meter device comprises inline filters to protect critical flow orifices. Also, the meter device may regulate the flow of gas both into, and out of, a plurality of reactor vessels.

BRIEF DESCRIPTION OF THE DRAWINGS

The invention is hereinafter described with reference to the accompanying drawings in which:

FIG. 1 is a schematic representation of the system for purifying a gas with a sensing (safety) device to prevent damage to the reactor vessel (and most particularly) its contents in accordance with this invention; and FIG. 2 is a schematic representation of the flow meter utilizing critical flow orifices protected by inline filters in accordance to this invention.

DESCRIPTION OF THE PREFERRED EMBODIMENT

The major advantage of the present invention is that it reduces the number of measuring devices required to safeguard a purifier from impurities appearing in the gas stream under both the normal flow and backflow conditions. This increases system reliability and reduces cost. It also potentially reduces the amount of sample gas withdrawn from the system. This gas, sent to the measuring device, is typically sent to vent and thus represents loss of product gas. This advantage will be greater on small units since the amount of gas required by the safety device is typically independent of the amount of gas passing through the purifier.

The current invention proposes to take samples of the feed stream both up and down stream of the getter. The streams are then combined and sent to a single gas analyzer. If the oxygen levels are above a selected level, the gas analyzer will alert that the system has too much oxygen. Any further gas flow will then be prevented, so impurities can be prevented from entering the purification system.

The current invention allows the sampling of streams up and downstream of a purifier by combining the two streams and analyzing for the reactive species in a single device. This is illustrated in FIG. 2. Sample streams are drawn upstream 4 and downstream 7 of the purifier. Impure sample stream 3 is fed into reactor vessel 1, which contains getter materials 2. Emerging from reactor vessel 1 is purified gas stream 6. Impure gas stream 3 splits into upstream impure gas stream 4, while purified gas stream 6 splits into downstream purified gas stream 7. Streams 4 and 7 pass through flow meters 22 and are combined to form combined stream 20, which passes into sensing device 21. Sensing device 21 (otherwise known as a safety device) measures the level of reactive species. Sensing device 21 is associated with control device 12. Again, if the level of reactive species is measured above a certain setpoint, action is taken to safeguard the bed. Such action may be to decrease the flow of the impure gas stream 3 from entering the reactive vessel 1. Gas passing though sensing device 21 will pass to vent 9.

This arrangement takes advantage of the fact that the exact metering of the reactive species is not necessary to safeguard the bed and that the level of reactive species necessary to damage the bed is typically orders of magnitude above that fed to the purifier. For example, nickel-based getter materials are used to remove oxygen from gaseous feed nitrogen that is to be supplied to semiconductor facilities. The feed nitrogen will typically have oxygen levels on the order of 1 ppm. Semiconductor facilities require the oxygen level to be on the order of 1 ppb, hence the use of the purifier. The level of oxygen that causes safety issues with the purifier bed is on the order of 1000 ppm. Thus, if a sensing device is used that alarms at 100 ppm, this is far greater than that seen during normal conditions and also well below the level that may constitute a problem for the bed. By combining the two streams, a new setpoint of 50 ppm can be chosen. Assuming that the sample streams from up and downstream of the purifier have the same flow rate, if either stream exceeds 100 ppm then the sensing device will alarm because the combined stream will have a level in excess of 50 ppm. In practice, one cannot be sure of metering the flows of the streams such that they are exactly equal. However, this is easily accounted for in the choice of setpoint based on conservative ranges of the degree to which the flow metering could be in error.

A gas stream containing about 0.1 ppm to about than 5 ppm of oxygen is considered the normal contaminant range; a gas stream containing about 45 to about 100 ppm of oxygen contaminant will likely cause the combined stream to fall outside the setpoint; and a gas stream containing greater than about 950 ppm of oxygen may cause damage to the reactive getter bed.

This illustrates the wide difference between normal contaminant levels and excessive levels, which is the justification for accepting the loss in accuracy associated with measuring a combined stream (caused by errors introduced through inexact metering) compared to measuring each stream individually.

The maximum discrepancy may be considered to be that one flow is twice that of the other. In this case, the worst case scenario is the stream that has high levels is the lower flow. By simple mass balance, setting the alarm at 33 ppm, instead of 100 ppm will ensure that neither stream ever exceeds 100 ppm. The lowest level of contaminants that could trigger the control action is 33 ppm (if present at those levels in both streams).

FIG. 1 is another embodiment of the present invention. FIG. 1 shows flow meter 22 having a particular as the flow metering means. It is believed that the most cost effective and reliable means of metering the flow is through the use of critical flow orifices 30. Critical flow orifice 30 with inline filter 31 upstream is placed in each of the sample streams prior to combination. The filter ensures that the orifice is not blocked by particulates. Critical flow orifices meter flow by restricting the flow such that sonic velocity occurs through the orifice. This typically requires that the pressure ratio across the orifice is greater than 2. It can be shown that both first impure gas 4 and purified gas 7 both pass through this specialized flow meter 22 to form combined gas stream 22. In most commercial applications, the pressure of the gas to be purified will be on the order of 90 psig or higher. Since the sensing device will normally operate at close to atmospheric pressure, the pressure ratio is sufficiently large (~>5) to ensure choked flow. The orifices can be sized by any standard means familiar to those skilled in the art. The mass flow through a critical flow orifice is roughly proportional to the upstream pressure. Since the pressure drop is typically small across the purifier compared to the absolute pressure, equal sized orifices may be used in most instances. The amount of flow of the combined stream should be at least sufficient to ensure proper operation of the sensing device. For example, oxygen analyzers typically require a flow on the order of 200 scc/min.

In an alternative embodiment, the present invention may be extended to a plurality of purifiers. For example, streams could be taken from stream and/or downstream of numerous purifiers and sent to a single sensing device. The setpoint for the combined stream should be set such that if any of the streams exceeds setpoint the sensing device would trigger action to safeguard the bed.

The sample stream flows could be controlled using flow measuring devices and control valves. This would ensure active control of the flow at the cost of expense. Flow switches in the sample streams could be employed to indicate a no-flow condition.

The safety device used could be a commercially available analyzer or a custom unit. One potential drawback to the design is that if the sensing device were allowed to build pressure then the potential exists for impure gas to bypass the purifier and enter the purified stream. (Gas passes from the sample stream 4 through metering means 22, through second metering means 22 and into the exit stream from the purifier through stream 7.) The potential for such contamination is minimal because the normal operating pressure of stream 20 is significantly lower than the pressure of lines 4 and 7. If the vent were blocked, the quantity of gas that can bypass is minimal since it has to flow through two flow metering devices. Additional means of protecting against this scenario is to place relief valves in line 20. This will vent the line if it approaches the operating pressure of the purifier. Alternatively or additionally, a check valve can be placed in line 7 that only allows flow to leave the purifier.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. A system for purifying a gas to produce a purified gas and protecting a reactor vessel in the system from damage comprising:
   a. a reactor vessel;
   b. a first impure gas passing through the reactor vessel;
   c. a second purified gas which emerges from the reactor vessel as a product;
   d. a sensing device configured to receive a first portion of the first impure gas and a second portion of the second purified gas;
   e. a plurality of metering devices to regulate the flow of the first impure gas and the second purified gas into combined gases and to direct the combined gases to the sensing device, whereby the sensing device analyzes the combined gases; and
   f. a control unit configured to receive information from the sensing device and to control the flow of the first impure gas through the reactor based on the information received.

2. The system of claim 1 further comprising a plurality of flow controlling devices to control the flow of the first impure gas and the second purified gas.

3. The system of claim 1 further comprises a plurality of pressure gauges for measuring the flow of the first impure gas and the second purified gas.

4. The system of claim 1 wherein the reactor vessel comprises a getter bed for purifying gases.

5. The system of claim 1 wherein the sensing device comprises an impurity monitor to measure the impurity in the first impure gas.

6. The system of claim 1 wherein the sensing device comprises a control device to regulate the flow of the first stream gas.

7. The system of claim 1 wherein contaminant gases removed from the reactor vessel comprises oxygen.

8. The system of claim 1 wherein the reactor vessel comprises a catalyst.

9. The system of claim 1 further comprising a plurality of flow meter devices to monitor the flow of gases.

10. The system of claim 9 wherein the flow meter devices comprises inline filters to protect critical flow orifices.

* * * * *